(12) United States Patent
Biedermann et al.

(10) Patent No.: US 11,992,244 B2
(45) Date of Patent: May 28, 2024

(54) POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/748,966

(22) Filed: May 19, 2022

(65) Prior Publication Data

US 2022/0346842 A1    Nov. 3, 2022

Related U.S. Application Data

(63) Continuation of application No. 16/169,785, filed on Oct. 24, 2018, now Pat. No. 11,369,418.

(Continued)

(30) Foreign Application Priority Data

Oct. 25, 2017   (EP) .................................... 17198406

(51) Int. Cl.
*A61B 17/70* (2006.01)
*A61B 17/86* (2006.01)
*A61B 17/56* (2006.01)

(52) U.S. Cl.
CPC ...... *A61B 17/7037* (2013.01); *A61B 17/7032* (2013.01); *A61B 17/7076* (2013.01);

(Continued)

(58) Field of Classification Search
CPC .......... A61B 17/70; A61B 17/7032–34; A61B 17/7076; A61B 17/7086; A61B 17/8605; A61B 17/86
See application file for complete search history.

(56) References Cited

U.S. PATENT DOCUMENTS 5,217,497 A    6/1993   Mehdian
5,375,956 A    12/1994  Pennig
(Continued)

FOREIGN PATENT DOCUMENTS

EP   2 591 738 A1   5/2013
EP   3 092 962 A1   11/2016
(Continued)

OTHER PUBLICATIONS

Extended European Search Report for Application No. 17198406.5, dated May 7, 2018, 9 pages.
(Continued)

*Primary Examiner* — Tessa M Matthews
(74) *Attorney, Agent, or Firm* — Lewis Roca Rothgerber Christie LLP (57) ABSTRACT

A bone anchoring device includes a receiving part for coupling a rod to a bone anchoring element, the receiving part having a first end, a second end, a recess at the first end for receiving the rod, and a compressible head receiving portion at the second end for accommodating a head of the bone anchoring element, a pressure member positionable in the receiving part to exert pressure on the head, and a clamping ring positionable around the head receiving portion and movable towards the first end of the receiving part to a locking position where the clamping ring exerts force on and compresses the head receiving portion. In the locking position, at least part of the clamping ring that faces the first end of the receiving part is exposed to the outside to (Continued)

facilitate movement of the clamping ring away from the first end of the receiving part.

24 Claims, 9 Drawing Sheets

Related U.S. Application Data (60) Provisional application No. 62/576,961, filed on Oct. 25, 2017.

(52) U.S. Cl.
CPC ...... *A61B 17/7086* (2013.01); *A61B 17/8605* (2013.01); *A61B 2017/564* (2013.01)

(56) References Cited

U.S. PATENT DOCUMENTS

| | | | |
|---|---|---|---|
| 5,549,608 | A | 8/1996 | Errico |
| 5,575,792 | A | 11/1996 | Errico |
| 5,586,984 | A | 12/1996 | Errico |
| 5,672,176 | A | 9/1997 | Biedermann et al. |
| 5,728,098 | A | 3/1998 | Sherman et al. |
| 6,254,602 | B1 | 7/2001 | Justis |
| 6,273,888 | B1 | 8/2001 | Justis |
| 6,299,616 | B1 | 10/2001 | Beger |
| 6,582,436 | B2 | 6/2003 | Schlapfer et al. |
| 6,743,231 | B1 | 6/2004 | Gray et al. |
| 7,947,065 | B2 | 5/2011 | Hammill, Sr |
| 7,955,359 | B2 | 6/2011 | Matthis et al. |
| 7,967,826 | B2 | 6/2011 | Colleran et al. |
| 7,988,694 | B2 | 8/2011 | Barrus et al. |
| 8,075,603 | B2 | 12/2011 | Hammill, Sr. |
| 8,298,275 | B2 | 10/2012 | Rezach |
| 8,506,609 | B2 | 8/2013 | Biedermann et al. |
| 8,506,610 | B2 | 8/2013 | Biedermann |
| 8,636,781 | B2 | 1/2014 | Biedermann |
| 9,005,260 | B2 | 4/2015 | Dauster et al. |
| 9,050,148 | B2 | 6/2015 | Jackson |
| 9,144,441 | B2 | 9/2015 | Biedermann et al. |
| 9,173,684 | B2 | 11/2015 | Biedermann et al. |
| 9,333,016 | B2 | 5/2016 | Biedermann et al. |
| 9,681,895 | B2 | 6/2017 | Biedermann et al. |
| 9,895,171 | B2 | 2/2018 | Webb |
| 2004/0254576 | A1 | 12/2004 | Dunbar, Jr. et al. |
| 2005/0080415 | A1 | 4/2005 | Keyer et al. |
| 2005/0096653 | A1 | 5/2005 | Doubler et al. |
| 2005/0228385 | A1 | 10/2005 | Iott |
| 2006/0074445 | A1 | 4/2006 | Gerber et al. |
| 2006/0111715 | A1 | 5/2006 | Jackson |
| 2006/0173454 | A1 | 8/2006 | Spitler et al. |
| 2006/0247658 | A1 | 11/2006 | Pond |
| 2007/0161987 | A1 | 7/2007 | Capote |
| 2007/0233078 | A1 | 10/2007 | Justis et al. |
| 2007/0270842 | A1 | 11/2007 | Bankoski |
| 2008/0015576 | A1 | 1/2008 | Whipple |
| 2008/0108992 | A1 | 5/2008 | Barry et al. |
| 2008/0161859 | A1 | 7/2008 | Nilsson |
| 2009/0036934 | A1 | 2/2009 | Biedermann et al. |
| 2009/0062860 | A1 | 3/2009 | Frasier |
| 2009/0069852 | A1 | 3/2009 | Farris et al. |
| 2009/0105715 | A1 | 4/2009 | Belliard |
| 2009/0105756 | A1 | 4/2009 | Richelsoph |
| 2009/0149887 | A1 | 6/2009 | Schlaepfer et al. |
| 2010/0030135 | A1 | 2/2010 | Mitchell |
| 2010/0131017 | A1 | 5/2010 | Farris et al. |
| 2010/0160977 | A1 | 6/2010 | Gephart et al. |
| 2010/0168800 | A1 | 7/2010 | Biedermann et al. |
| 2010/0204735 | A1 | 8/2010 | Gephart et al. |
| 2011/0009911 | A1 | 1/2011 | Hammill, Sr. et al. |
| 2011/0040336 | A1 | 2/2011 | Hammill, Sr. et al. |
| 2011/0060374 | A1 | 3/2011 | Sicvol et al. |
| 2011/0125196 | A1 | 5/2011 | Quevedo et al. |
| 2011/0160779 | A1 | 6/2011 | Schlaepfer et al. |
| 2011/0213424 | A1 | 9/2011 | Biedermann et al. |
| 2011/0276098 | A1 | 11/2011 | Biedermann et al. |
| 2012/0046699 | A1 | 2/2012 | Jones et al. |
| 2012/0059426 | A1 | 3/2012 | Jackson |
| 2012/0095516 | A1 | 4/2012 | Dikeman |
| 2012/0179209 | A1 | 7/2012 | Biedermann et al. |
| 2012/0179211 | A1 | 7/2012 | Biedermann et al. |
| 2012/0203288 | A1 | 8/2012 | Lange et al. |
| 2012/0209332 | A1 | 8/2012 | Janowski |
| 2013/0085536 | A1 | 4/2013 | Biedermann et al. |
| 2013/0096623 | A1 | 4/2013 | Biedermann et al. |
| 2013/0110179 | A1 | 5/2013 | Barrus et al. |
| 2013/0123860 | A1 | 5/2013 | Biedermann et al. |
| 2013/0123861 | A1 | 5/2013 | Biedermann et al. |
| 2013/0165977 | A1* | 6/2013 | Biedermann ...... A61B 17/7032 606/279 |
| 2014/0031880 | A1* | 1/2014 | Biedermann ...... A61B 17/7035 606/305 |
| 2014/0214097 | A1 | 7/2014 | Jackson et al. |
| 2014/0358182 | A1 | 12/2014 | Puekert |
| 2015/0119940 | A1* | 4/2015 | Jackson ............. A61B 17/7076 606/266 |
| 2015/0182265 | A1 | 7/2015 | Biedermann et al. |
| 2016/0030090 | A1 | 2/2016 | Webb |
| 2016/0220281 | A1 | 8/2016 | Biedermann et al. |
| 2016/0331412 | A1 | 11/2016 | Biedermann et al. |
| 2017/0020574 | A1 | 1/2017 | Biedermann et al. |
| 2018/0055542 | A1 | 3/2018 | Biedermann |
| 2019/0192192 | A1 | 6/2019 | Biedermann et al. |
| 2019/0274737 | A1 | 9/2019 | Biedermann et al. |

FOREIGN PATENT DOCUMENTS

| | | |
|---|---|---|
| EP | 3 120 791 A1 | 1/2017 |
| EP | 3 184 063 A1 | 6/2017 |
| JP | 2007-506525 A | 3/2007 |
| JP | 2009-544414 A | 12/2009 |
| WO | WO 2005/030070 A1 | 4/2005 |
| WO | WO 2011/043799 A1 | 4/2011 |
| WO | WO 2011/077511 A1 | 6/2011 |
| WO | WO 2015/069873 A1 | 5/2015 |

OTHER PUBLICATIONS

European Search Report for European Application No. 16182818.1, European Search Report dated Jan. 18, 2017 and dated Jan. 25, 2017 (8 pages).

* cited by examiner

Fig. 21 ically disposed, a recess formed in its side for receiving the rod of the implant apparatus, and an exterior threading disposed on its upper portion for receiving thereon a top locking nut. A locking ring is disposed about the exterior of the lower portion of the coupling element and provides an inward force on the outwardly tapered portion upon downward translation thereof, thereby causing the interior chamber to crush lock the screw head therein.

POLYAXIAL BONE ANCHORING DEVICE

CROSS-REFERENCE TO RELATED APPLICATION(S)

This application is a continuation of U.S. patent application Ser. No. 16/169,785, filed Oct. 24, 2018, which claims priority to and the benefit of U.S. Provisional Patent Application No. 62/576,961, filed Oct. 25, 2017, the contents of which are hereby incorporated by reference in their entirety, and claims priority from European Patent Application EP 17 198 406.5, filed Oct. 25, 2017, the contents of which are hereby incorporated by reference in their entirety.

BACKGROUND

The invention relates to a polyaxial bone anchoring device. More specifically, the bone anchoring device includes a receiving part for coupling a rod to a bone anchoring element that has a head to be received in the receiving part, and further includes a clamping ring that is configured to lock and unlock the head in the receiving part, for example by using an instrument.

DESCRIPTION OF RELATED ART

U.S. Pat. No. 5,549,608 describes a polyaxial orthopedic device for use with a rod implant apparatus including a screw having a curvate head and a coupling element. The coupling element has a tapered portion including a slotted interior chamber in which the curvate head is initially polyaxially disposed, a recess formed in its side for receiving the rod of the implant apparatus, and an exterior threading disposed on its upper portion for receiving thereon a top locking nut. A locking ring is disposed about the exterior of the lower portion of the coupling element and provides an inward force on the outwardly tapered portion upon downward translation thereof, thereby causing the interior chamber to crush lock the screw head therein.

US 2005/0096653 A1 describes a low-profile orthopedic device used to fix and stabilize bones to correct anomalies in skeletal structure. The device includes a bone screw and a clamp movably attached to the screw. The clamp includes a compression ring. A connecting rod connects several screws through slots in the clamps. In one embodiment a set screw is used for holding the rod and the clamp together. After the rod is passed through the clamp the compression ring is moved to the closed position locking the orientation of the rod and the screw.

US 2013/0085536 A1 describes a polyaxial bone anchoring device including a receiving part with a rod receiving portion and a head receiving portion for introducing and clamping of the head of a bone anchoring element, and a locking ring configured to be arranged around the head receiving portion. The locking ring includes an engagement structure for engagement with a tool to allow the locking ring to be moved out of the locking position, i.e., releasing the locking mechanism. This enables a surgeon or other practitioner to carry out revisions or further positioning or re-positioning of the angular position of the receiving part with respect to the bone anchoring element.

SUMMARY

In spinal surgery, often multiple segments of the spinal column have to be corrected and/or stabilized using a spinal rod and polyaxial bone anchors. During such a procedure, repeated adjustments of a bone anchoring element and the rod relative to a receiving part of a polyaxial bone anchoring device may become necessary.

It is an object of the invention to provide a polyaxial bone anchoring device that allows for improved handling during surgery.

According to an embodiment, the bone anchoring device includes a receiving part for coupling a rod to a bone anchoring element, the receiving part having a first end, a second end, a central axis extending between the first end and the second end, a recess at the first end for receiving a rod, and a head receiving portion at the second end for accommodating a head of a bone anchoring element, the head receiving portion being at least partially flexible, a pressure member configured to exert pressure on an inserted head, and a clamping ring configured to be arranged around the head receiving portion, wherein a translation of the clamping ring towards the first end provides a force that causes the head receiving portion to be compressed.

According to another embodiment, the bone anchoring device includes a receiving part for coupling a rod to a bone anchoring element, the receiving part having a first end, a second end, a central axis extending between the first end and the second end, a recess at the first end for receiving a rod, and a head receiving portion at the second end for accommodating a head of a bone anchoring element, the head receiving portion being at least partially flexible, and a clamping ring configured to be arranged around the head receiving portion, wherein a translation of the clamping ring towards the first end provides a force that causes the head receiving portion to be compressed, wherein by means of the recess two upstanding legs are formed, wherein the legs have a first portion and a second portion positioned between the second end of the receiving part and the first portion, and wherein the first portion is separable from the second portion.

According to embodiments of the invention, the bone anchoring element can be locked relative to the receiving part in an angular position and can be unlocked independently from the fixation of the rod.

The locking of the head is effected by moving the clamping ring upwards, i.e., towards the first end of the receiving part, and the releasing of the head is effected by moving the clamping ring downwards, i.e., towards the second end of the receiving part. Moving the clamping ring upwards for locking may have the clinical advantage of avoiding exertion of pressure onto the vertebrae when locking the head. Moreover, moving the clamping ring upwards for locking requires less space at the second or bottom end of the receiving part. Thereby, the second end of the receiving part can be placed closer to the bone surface.

When a pressure member is provided for exerting pressure onto the head, the clamping force may be distributed onto the head more effectively. Moreover, by locking the rod, pressure exerted by the rod onto the pressure member may further increase the locking force onto the head.

The separable first portion of the legs of the receiving part form extended tabs that allow convenient manipulation of the polyaxial bone anchoring device during surgery. Furthermore, the extended tabs may permit guiding and/or supplying elements of an implant or instruments to the implantation site. This is particularly useful in the case of minimally invasive surgery (MIS).

The locking and unlocking of the bone anchoring element during surgery can also be carried out with the rod being not yet inserted or being at an elevated position in the receiving part away from the bottom of the rod receiving recess.

An instrument for locking and unlocking the head via the clamping ring can be used when the rod and the fixation element are already inserted into the channel of the receiving part, but when the rod is not yet fixed. Thus, a temporary locking of the bone anchoring element in the receiving part can be effected with the instrument. When the head of the bone anchoring element is locked in the receiving part and the rod is still movable, it is possible to pull the bone anchoring device with an instrument towards the inserted rod and thereby also to pull the associated vertebrae towards the rod for correcting a position of the vertebrae. Therefore, the polyaxial bone anchoring device permits various adjustments and re-adjustments of the angular position and/or rod position during surgery.

The polyaxial bone anchoring device according to an embodiment permits insertion of the bone anchoring element first in the bone, and thereafter mounting the receiving part with the clamping ring onto the head of the bone anchoring element. Moreover, with a polyaxial bone anchoring device according to embodiments of the invention, a modular system can be provided that allows for combining of various anchoring elements with the receiving part on demand, depending on the actual clinical requirements. This reduces the overall costs of using polyaxial screws, reduces inventory, and gives the surgeon a wider or more versatile choice of implants.

BRIEF DESCRIPTION OF THE DRAWINGS

Further features and advantages of the invention will become apparent from the description of embodiments by means of the accompanying drawings. In the drawings:

FIG. 18b shows an enlarged view of a detail of FIG. 18a.

DETAILED DESCRIPTION

As shown in FIGS. 1 to 4, a bone anchoring device according to an embodiment of the invention includes a bone anchoring element 1 in the form of, for example, a bone screw having a shank 2 with a threaded portion and a head 3 with a spherically-shaped outer surface portion. The head 3 may have a recess 4 for engagement with a driver or tool. The bone anchoring device also includes a receiving part 5 for receiving a rod 6 to be connected to the bone anchoring element 1. Further, a pressure member 7 may be provided in the receiving part 5 for exerting pressure onto the head 3 of the bone anchoring element 1. In addition, the bone anchoring device includes a clamping ring 8 that is mountable to the receiving part 5 for compressing a portion of the receiving part 5 to exert pressure onto the pressure member 7 and in turn onto the head 3. Lastly, the bone anchoring element also includes a fixation element 9 in the form of, for example, an inner screw or set screw for fixing the rod 6 in the receiving part 5.

The receiving part 5 will be described in greater detail, referring additionally to FIGS. 5 to 8. The receiving part 5 includes a first end 5a and an opposite second end 5b and a central axis C that passes through the first end 5a and the second end 5b. A passage 51 extends through the receiving part 5 from the first end 5a to the second end 5b. The passage 51 may be formed as a coaxial bore 51a in a region from the first end 5a to a distance from the first end 5a. Moreover, the passage 51 may widen into an accommodation space 51b with a maximum inner diameter that is greater than a maximum inner diameter of the coaxial bore 51a. The accommodation space 51b serves for accommodating the head 3 of the bone anchoring element 1 and at least a portion of the pressure member 7. At or close to the second end 5b, the accommodation space 51b narrows in a narrowing portion 51c towards the second end 5b. The narrowing portion 51c can be tapered, more specifically conically tapered, or can narrow in another shape.

A recess 52 that may be substantially U-shaped extends form the first end 5a in the direction of the second end 5b, wherein a width of the recess 52 is slightly larger than a diameter of the rod 6, such that the rod 6 can be placed in the recess 52 and can be guided therein. Hence, the recess 52 forms a channel for the rod 6. By means of the recess 52, two free legs 52a 52b are formed, on which an internal thread 53 may be provided. The internal thread 53 can be, for example, a metric thread, a flat thread, a negative angle-thread, a saw-tooth thread, or any other thread form. Preferably, a thread form such as a flat thread or a negative angle thread is used to prevent or reduce splaying of the legs 52a, 52b when the fixation element 9 is screwed-in.

At a distance from the first end 5a, a break-away or break-off portion in the form of a circumferential groove 5c is provided that permits breaking off of a portion of the legs 52a, 52b above the groove 5c. The groove divides the legs 52a, 52b into a first or upper portion 520a, 520b extending above the groove 5c and a second or lower portion 521a, 521b extending below the groove 5c to a base of the recess 52. At the groove 5c, a wall thickness of the legs 52a, 52b may be reduced in such a manner that the upper portion 520a, 520b of the legs may be broken away from the lower portion 521a, 521b. Hence the upper portions 520a, 520b, respectively, form extended tabs. Any other means for permitting breaking-away the upper portions 520a, 520b from the lower portions 521a, 521b may be contemplated, such as, for example, perforations, etc. The groove 5c may have downwardly inclined upper and/or lower walls 5c' that may provide safe engagement with a tool.

The internal thread 53 is provided along at least a portion of the upper portion 520a, 520b and of the lower portion 521a, 521b of the legs 52a, 52b so that the fixation element 9 can be screwed down along the pathway defined by the bore 51a. The depth of the recess 52 is such that when the rod 6 is placed into the recess 52 and the fixation element 9 is screwed between the legs 52a, 52b, the fixation element 9 does not substantially protrude out the receiving part 5 when the upper portion 520a, 520b of the legs have been broken off. The extended tabs provided by the upper portion 520a, 520b of the legs can be used to define a pathway, for example in MIS, to guide an implant component, for example the rod 6 or the fixation element 9 to the bone anchor 1 at the implantation site beneath the skin of the patient.

Figure 1:
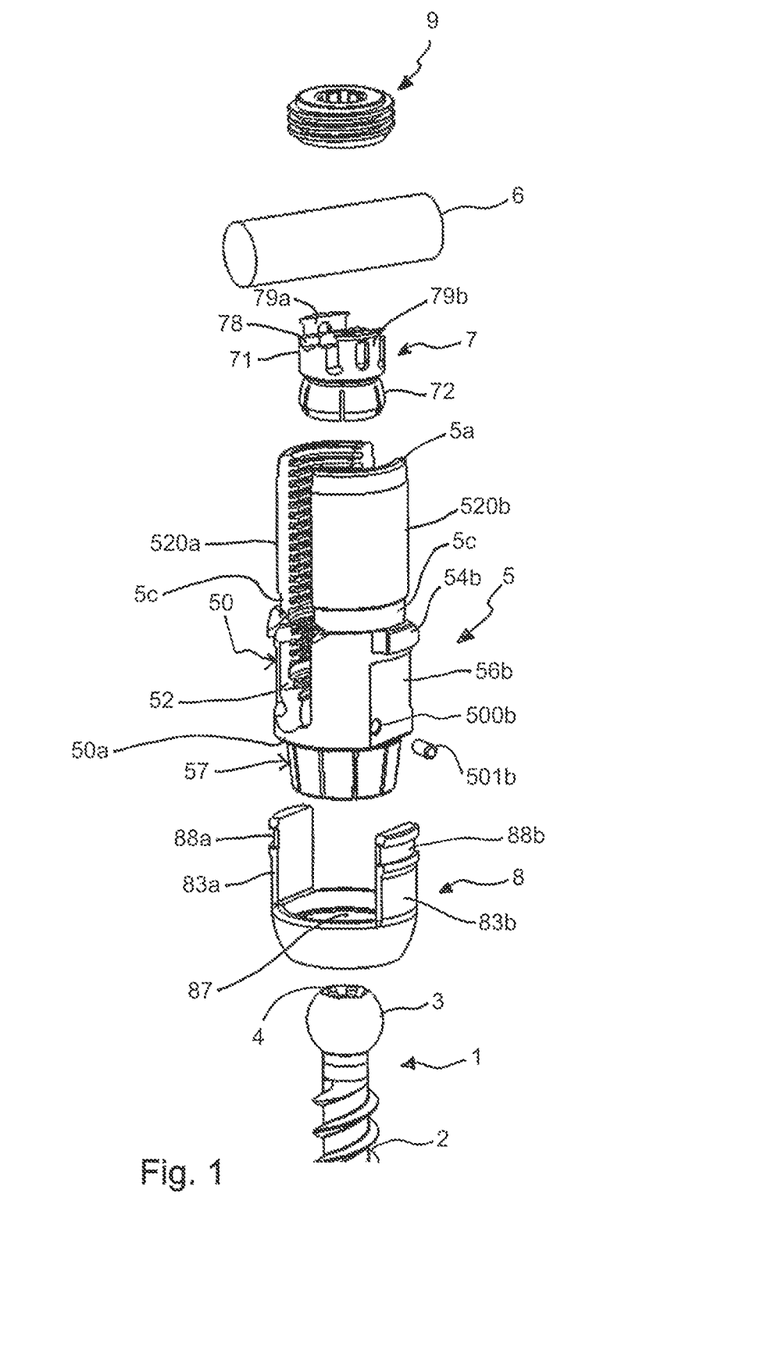
FIG. 1 shows an exploded perspective view of an embodiment of a polyaxial bone anchoring device.
Figure 2:
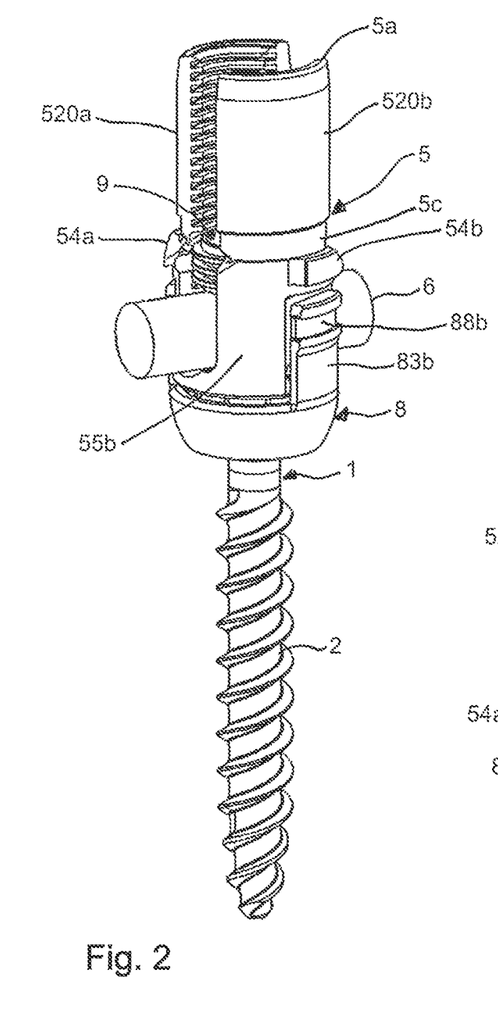
FIG. 2 shows a perspective view of the polyaxial bone anchoring device of FIG. 1 in an assembled state.
Figure 3:
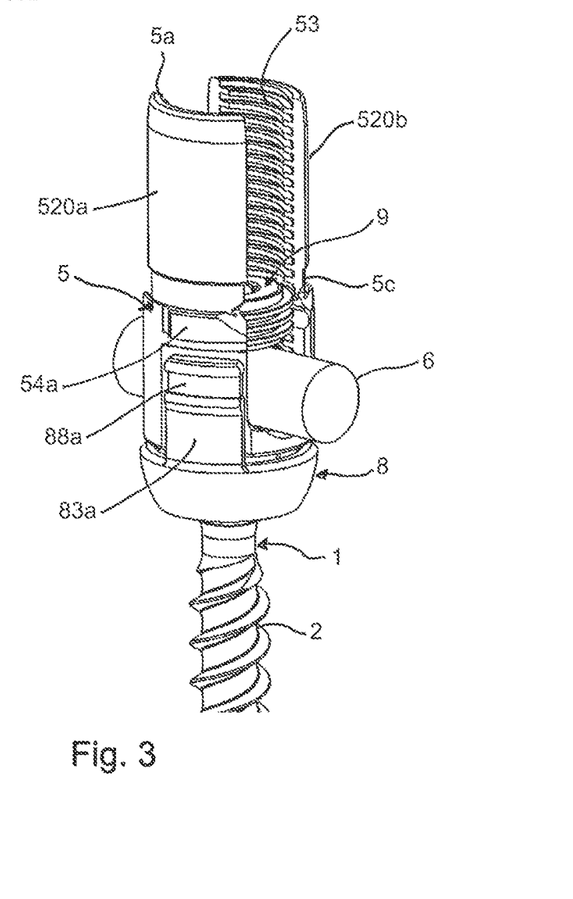
FIG. 3 shows a further perspective view of the polyaxial bone anchoring device of FIG. 1 in an assembled state.
Figure 4:
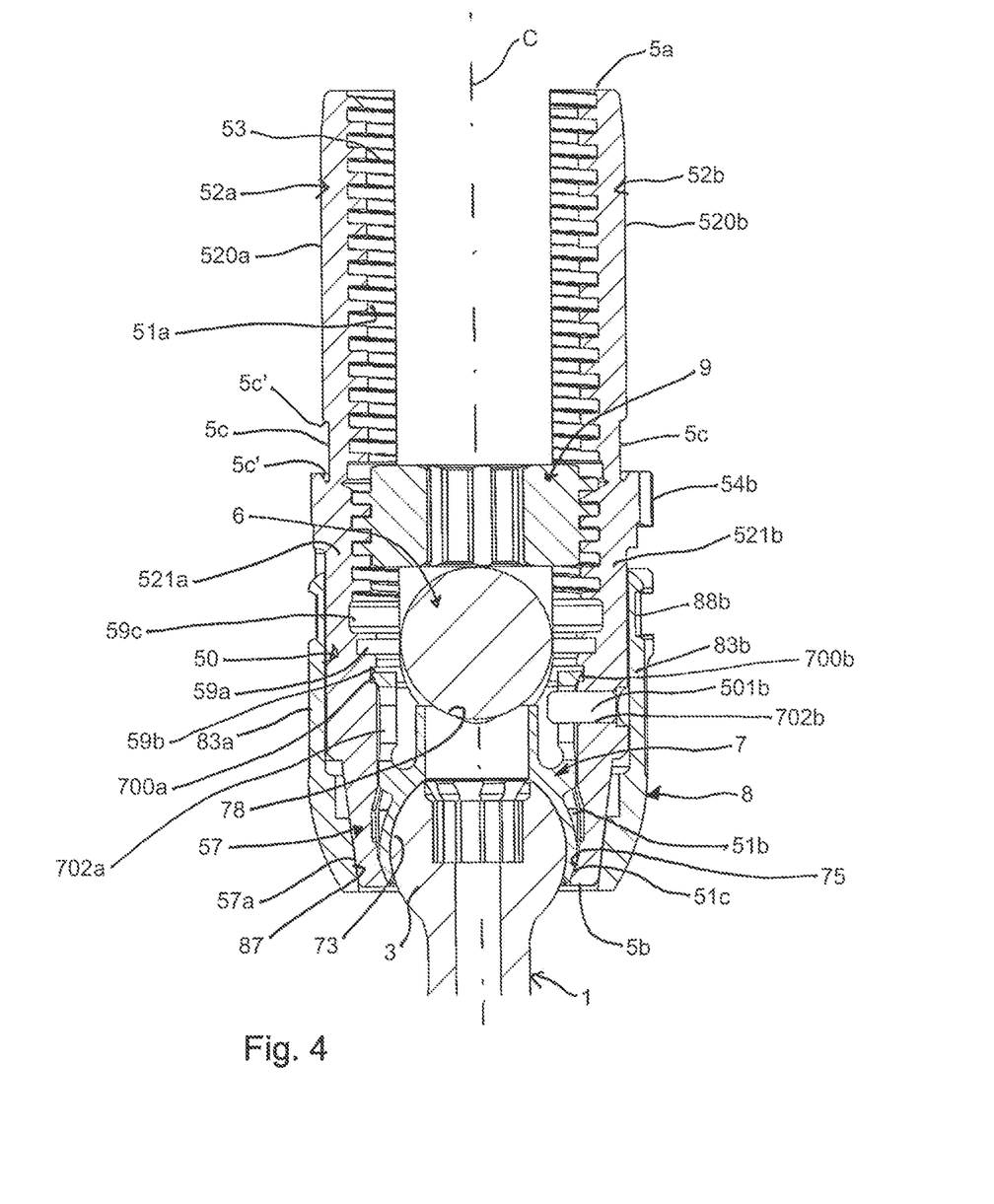
FIG. 4 shows a cross-sectional view of the polyaxial bone anchoring device of FIGS. 1 to 3, wherein the cross-section has been taken in a plane perpendicular to an axis of an inserted rod and extending through a center of a receiving part of the polyaxial bone anchoring device.
Figure 5:
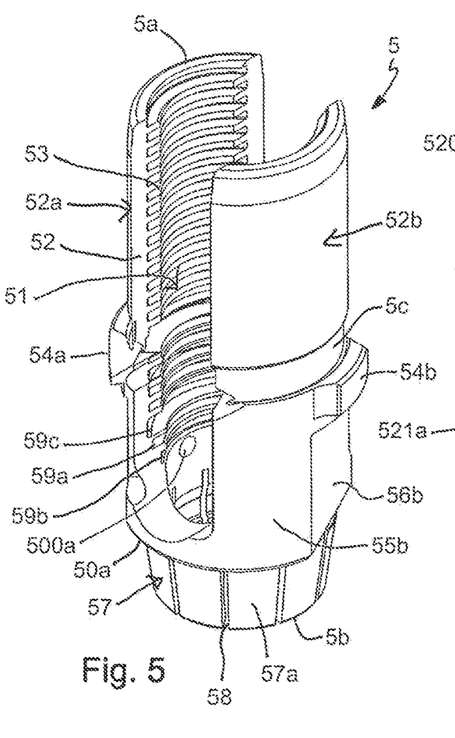
FIG. 5 shows a perspective view from the top of the receiving part of the polyaxial bone anchoring device of FIGS. 1 to 4.
Figure 6:
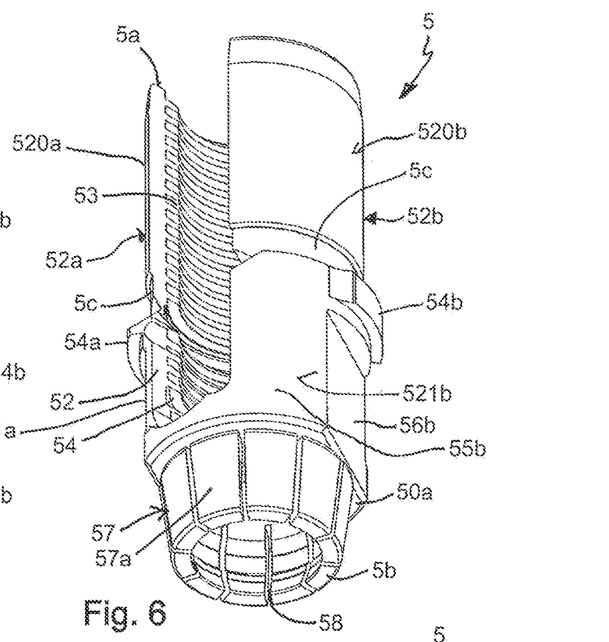
FIG. 6 shows a perspective view from the bottom of the receiving part of FIG. 5.
Figure 7:
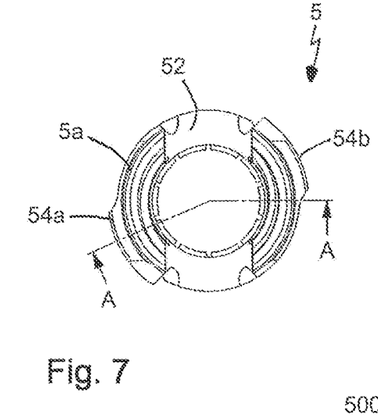
FIG. 7 shows a top view of the receiving part of FIGS. 5 and 6.
Figure 8:
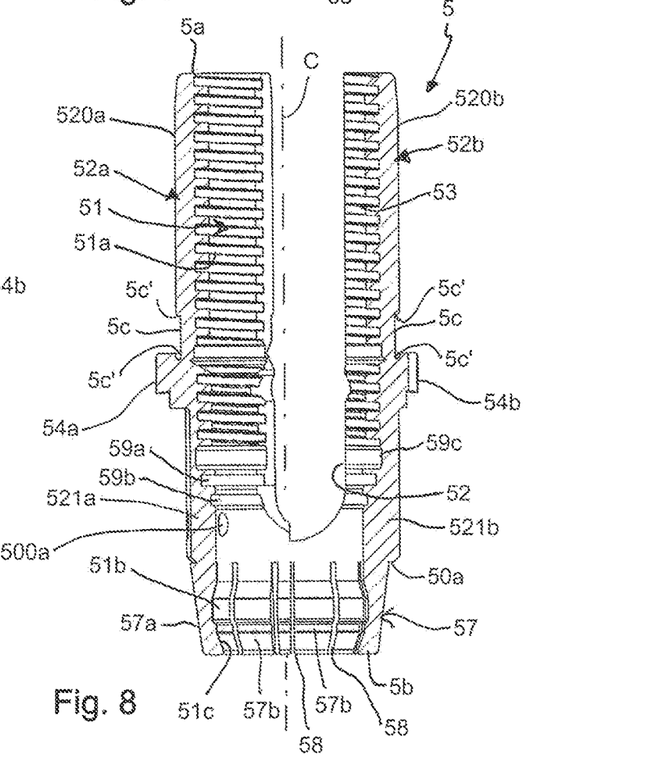
FIG. 8 shows a cross-sectional view of the receiving part of FIGS. 5 to 7, the cross-section taken along line A-A in FIG. 7.
Figure 9:
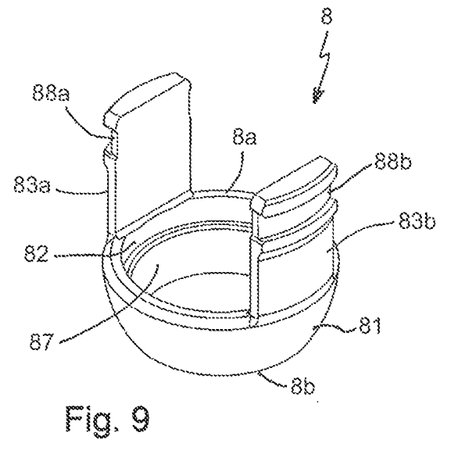
FIG. 9 shows a perspective view from the top of a clamping ring of the polyaxial bone anchoring device of FIGS. 1 to 4.
Figure 10:
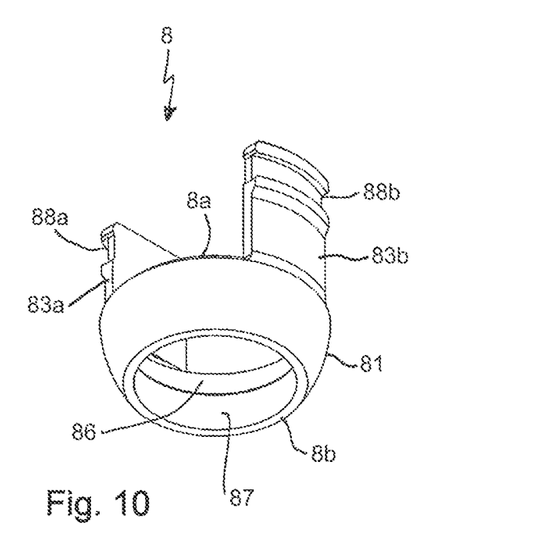
FIG. 10 shows a perspective view from the bottom of the clamping ring of FIG. 9.
Figure 11:
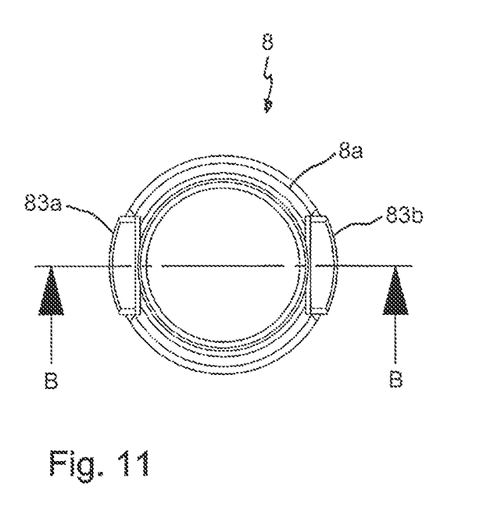
FIG. 11 shows a top view of the clamping ring of FIGS. 9 and 10.

As shown in more detail in FIGS. 4 and 8, on the inner wall of the passage 51 two stops are provided for the pressure member 7. A first stop is formed by an upper wall of a first circumferential groove 59a located below the thread 53. The first stop prevents upward movement of the pressure member 7 when the head 3 is inserted. A second stop is formed by a second circumferential groove 59b located at a distance from the first groove 59a in direction toward the lower end 5b. The second stop prevents upward movement of the pressure member 7 when the pressure member 7 is in a lower position, notably a pre-locking position as described in more detail below. Additionally, an undercut 59c may be provided at the lower end of the internal thread 53.

An upper part 50 of the receiving part 5, which includes the legs 52a, 52b, forms a rod receiving portion of the receiving part 5. Furthermore, in the wall of the receiving part 5, more specifically, in the wall of the upper part 50, at least one, preferably two holes 500a, 500b may be provided that may serve for inserting securing members, such as pins 501a, 501b to engage the pressure member 7. The holes 500a, 500b may be provided at substantially 90° from the rod receiving recess 52 and opposite to each other with respect to the longitudinal axis L of the recess 52.

The upper part 50 has a substantially cylindrical outer surface. An engagement structure for engagement with the instrument is provided at the outer surface, wherein the engagement structure may be formed by circumferential ribs 54a, 54b. In the embodiment shown, on each leg 52a, 52b there is one rib 54a, 54b, respectively. The ribs 54a, 54b are positioned between the groove 5c and a lower end 50a of the upper part 50. Each of the ribs 54a, 54b extends over a segment of the circumference of the upper part 50, for example, for approximately a quarter circle or less than a quarter circle (see, e.g., FIGS. 5 and 7). The arrangement is such that one end of each rib 54a, 54b is positioned at the recess 52 and the other end of each rib extends approximately to the middle of each leg 52a, 52b. Hence, in a circumferential direction, there is a rib-free surface portion 55a, 55b on the outer surface of each leg 52a, 52b, respectively. Furthermore, the ribs 54a, 54b are arranged in an asymmetric manner with respect to a plane extending through the central axis C and a longitudinal axis of the recess 52. More specifically, the position of the ribs 54a, 54b is offset by 180° measured in relation to the central axis C and is rotated with respect to the central axis C, such that the rib 54a of the leg 52a extends to the rod receiving recess 52 at one side of the receiving part 5 and the rib 54b extends to the rod receiving recess 52 at the other side of the receiving part 5. This permits an instrument to be placed first onto the rib-free portions 55a, 55b and then to be rotated to engage the ribs 54a, 54b. The ribs 54a, 54b may have a substantially rectangular cross-section and may have beveled end portions in the circumferential direction. It shall be understood that the number of ribs on each leg 54a, 54b is not limited to one single rib, but more than one rib on each leg 52a, 52b may be present, for example, in an axial direction. Also the shape of the ribs may be different in other embodiments. Instead of ribs or in addition to the ribs, grooves or other engagement structures may be provided.

The ribs are close to an upper end of the receiving part when the upper portions 520a, 520b of the legs 52a, 52b have been broken off. This allows the bone anchoring device to be engaged by an instrument at a position remote from the bone surface, which avoids damages to the body tissue.

The outer surface of the receiving part 5 also includes substantially flat or planar recessed portions 56a, 56b. The recessed portions 56a, 56b are positioned at the upper part 50 in a circumferential position that corresponds to the circumferentially extending ribs 54a, 54b and extend from an edge 50a at a bottom end of upper part 50 in a direction parallel to the central axis C up to a predetermined distance from the ribs 54a, 54b. The purpose of the recessed portions 56a, 56b may be to provide a guiding surface for upwardly projecting arms of the clamping ring 8, as will be detailed below. The recessed portions 56a, 56b need not have a planar flat surface recessed from a cylindrical outer contour of the receiving part 5 as in the embodiment, but may also be rounded and/or provided with side walls or can have any shape that is adapted to permit a guiding engagement with the arms of the clamping ring 8.

Between the upper part 50 and the second end 5b of the receiving part, a head receiving portion 57 of the receiving part 5 is provided that includes the accommodation space 51b. An outer surface portion, preferably the entire outer surface, of the head receiving portion 57 is substantially conically-shaped and tapers and narrows towards the second end 5b of the receiving part 5. A largest outer width of the head receiving portion is smaller than a width of the receiving part 5 at the lower end 50a of the upper part 50, so that the lower end 50a forms a shoulder.

The head receiving portion 57 is flexible. In particular, it is compressible upon action of a force that is directed towards the central axis C. In the embodiment shown, the head receiving portion 57 includes a plurality of flexible wall sections 57b that are separated by slits 58 extending in a longitudinal direction and being open towards the second end 5b. The number and size of the slits 58 is selected depending on the desired flexibility of the head receiving portion 57. An inner diameter of the passage 51 at the second end 5b is such that the head 3 can be inserted from the second end 5b.

The clamping ring 8 will be described in greater detail, referring additionally to FIGS. 9 to 12.

The clamping ring 8 has an upper end or first end 8a and an opposite lower end or second end 8b, and may have a substantially spherical outer surface 81 which narrows towards the second end 8b. The outer diameter of the spherical surface 81 at or adjacent to the first end 8a may be such that when the clamping ring 8 is mounted around the head receiving portion 57 of the receiving part 5, the outer spherical surface 81 of the clamping ring and the outer cylindrical surface of the upper part 50 of the receiving part 5 are flush with each other as depicted, for example, in FIGS. 2 and 3. An inner diameter of the clamping ring 8 is such that the clamping ring 8 can be mounted around the head receiving portion 57, wherein the upper end 8a faces towards the bottom end or edge 50a of the upper part 50 of the receiving part 5. It shall be noted, however, that the shape of the outer surface of clamping ring 8 may be different in other embodiments. For example, the outer surface 81 may have a cylindrical shape or another shape.

Figure 12:
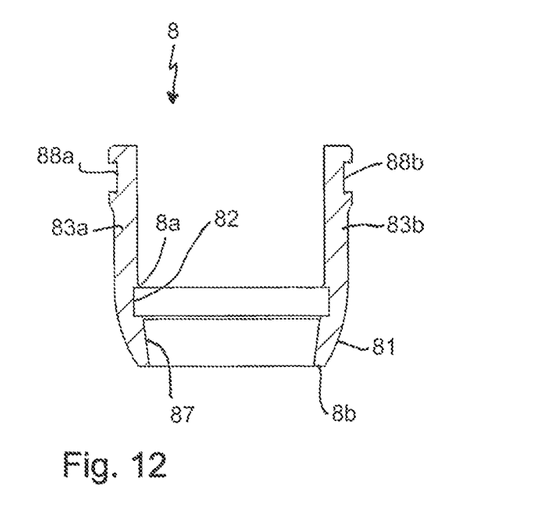
FIG. 12 shows a cross-sectional view of the clamping ring of FIGS. 9 to 11, the cross-section taken along line B-B in FIG. 11.
Figure 13:
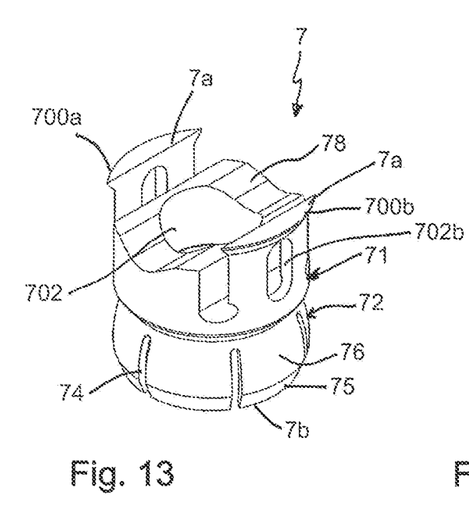
FIG. 13 shows a perspective view from the top of a pressure member of the polyaxial bone anchoring device of FIGS. 1 to 4.
Figure 14:
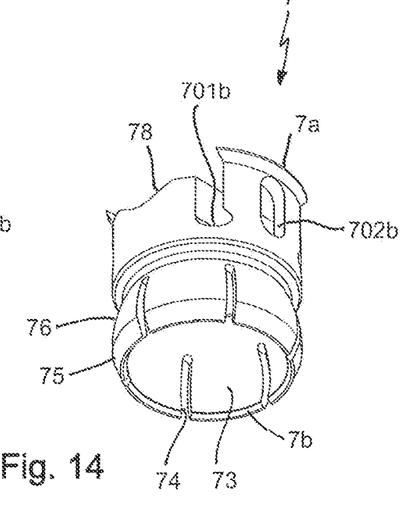
FIG. 14 shows a perspective view from the bottom of the pressure member of FIG. 13.
Figure 15:
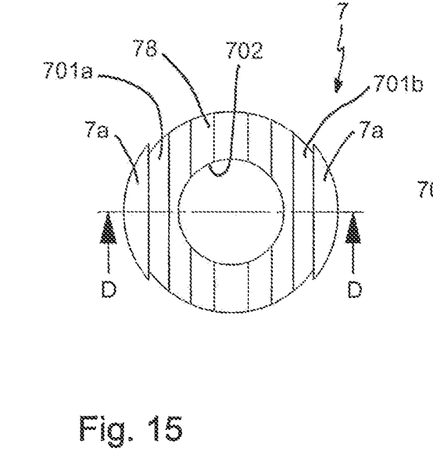
FIG. 15 shows a top view of the pressure member of FIGS. 13 and 14.
Figure 16:
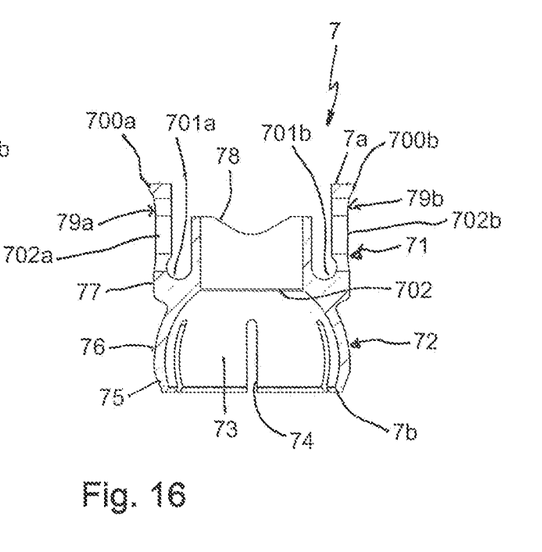
FIG. 16 shows a cross-sectional view of the pressure member of FIGS. 13 to 15, the cross-section taken along line D-D in FIG. 15.

As can be seen, in particular in FIG. 12, clamping ring 8 further has a first inner cylindrical surface portion 82 that is adjacent or substantially adjacent to the upper end 8a. Adjacent to or substantially adjacent to the lower end 8b, a second inner surface portion 87 of the clamping ring 8 may be tapered in such a manner that the inner diameter conically narrows towards the lower end 8b. The second inner surface portion 87 is configured to cooperate with the outer surface portion 57a of the head receiving portion of the receiving part. Preferably, the cone angle of the conical outer surface portion 57a corresponds to the cone angle of the conical inner surface portion 87 of the clamping ring. The cone angle may be selected such that self-locking may occur at least in a certain position of the clamping ring 8 when the clamping ring 8 is around the head receiving portion 57. The shape of the engaging surfaces of the head receiving portion 57 and the clamping ring 8 are such that when the clamping ring 8 is moved upwards on the head receiving portion 57, i.e., towards the upper end 5a of the receiving part, the cooperating surfaces 57a of the head receiving portion 57 and 87 of the clamping ring 8 exert an increasing inwardly directed radial force.

The clamping ring 8 further includes two upwardly projecting arms 83a, 83b extending from the first end 8a. The length of arms 83a, 83b substantially corresponds to a length of recessed portions 56a, 56b of the upper part 50 of the receiving part 5, which are arranged to slidably receive the arms 83a, 83b when the clamping ring 8 is attached to the receiving part, as shown, for example in FIG. 2. Similarly, the width of arms 83a, 83b substantially corresponds to that of recessed portions 56a, 56b. The two arms 83a, 83b are located diametrically opposite to each other.

Moreover, a height of the clamping ring 8 in an axial direction between the upper end 8a and the lower end 8b corresponds substantially to a height of the head receiving portion 57 of the receiving part 5, as shown, for example in FIG. 4.

Each of the upwardly projecting arms 83a, 83b includes an engagement structure for engagement with an instrument on its outer surface. The engagement structure may be formed at or close to a free end portion of the respective arm. In this embodiment, the engagement structure is provided as circumferentially extending notches or grooves 88a, 88b. As the engagement structure is provided at or close to a free end of the arms 83a, 83b, the engagement structure of the clamping ring 8 as well as the engagement structure of the receiving part 5 are located close to each other and away from the bone surface when the polyaxial bone anchoring device is in an assembled state in-situ. This arrangement requires less space within the body tissue for an instrument. A length of the engagement structures, e.g., the notches 88a, 88b, in a circumferential direction is limited to the width of the arms 83a, 83b and substantially corresponds to that of the engagement structures of the receiving part, i.e., the circumferential ribs 54a, 54b.

The arms 83a, 83b have such a length, that they fit into the recessed portions 56a, 56b, when the clamping ring is mounted around the head receiving portion 57. Preferably the free ends of the arms 83a, 83b do not abut against the lower side of the ribs 54a, 54b in any axial position of the clamping ring 8 so that the clamping ring 8 is freely movable in an axial direction between a lowermost position and an uppermost position and vice versa. The shape of the notches 88a, 88b can include a rectangular cross-section, a dovetail shape, or any other shape.

The pressure member 7 will be described in greater detail by referring additionally to FIGS. 13 to 16. The pressure member 7 includes an upper or first portion 71 with an upper end 7a and a lower or second portion 72 with a lower end 7b. The second portion 72 has a hollow interior 73 that may be substantially spherically-shaped to clamp the spherical head 3 therein. The flexible portion 72 is open at the second end 7b. A plurality of slits 74 extend from the lower end 7b through the second portion 72. The number and dimensions of the slits 74 are such that the wall of the second portion 72 is flexible enough to snap onto the head 3 when the head 3 is being inserted. An outer surface portion 75 adjacent to the lower end 7b of the pressure member 7 may be tapered, in particular conically tapered. The outer surface portion 75 is configured to cooperate with the inner surface portion 51c of the receiving part that is provided adjacent to the lower end 5b of the receiving part 5. It shall be understood that the outer surface portion 75 may narrow in another manner towards the lower end 7b. Another outer surface portion 76 of the second portion 72 of the pressure member 7 may be spherical segment-shaped as shown in the embodiment, so that the second portion is cap-like. It shall be noted that the outer surface can have any other shape, such as tapered or cylindrical or combinations of tapered, cylindrical, and spherical.

The first portion 71 of the pressure member 7 may have a substantially cylindrical outer surface 77 adjacent to the second portion 72. In the embodiment shown, the second portion 72 is recessed with respect to the cylindrical portion 77, however, any other shape may be possible. A rod support surface 78 may be provided in the first portion 71 that is configured to support an inserted rod 6. The rod support surface 78 may have a V-shaped cross-section in a direction transverse to the central axis C of the receiving part when the pressure member is in the receiving part, to permit support of rods of different diameters, but also can be flat or cylindrically or otherwise shaped.

The longitudinal axis of the rod support surface 78 extends transverse, in particular perpendicular, to the central axis C. To the left and to the right of the rod support surface 78 upstanding legs 79a, 79b are formed that have a substantially flat inner surface and a substantially cylindrical outer surface. The axial location of the rod support surface 78 in the direction of the central axis C may be closer to the free ends of the upstanding legs 79a, 79b than to their base, or half-way in-between. The upstanding legs 79a, 79b have outwardly directed portions 700a, 700b at their free ends, respectively. The outwardly directed portions 700a, 700b are configured to engage the groove 59a when the pressure member is in an insertion position. Between the rod support surface 78 and the upstanding legs 79a, 79b grooves 701a, 701b extending parallel to the rod support surface 78 are formed that render the legs 79a, 79b more flexible. The grooves 701a, 701b may have a circular segment-shaped cross-section. At the center of the upstanding legs 79a, 79b, axially elongated through-holes 702a, 702b may be provided, the longitudinal axes of which are parallel to the central axis C. The through-holes 702a, 702b may be adapted to be engaged by the pins 501a, 501b or other holding means to hold the pressure member 7 inside the receiving part 5, preferably to secure the pressure member 7 against rotation. To allow access to the head 3 with a driver or tool, a coaxial bore 702 may also be provided in the pressure member 7.

The dimensions of the pressure member 7 are such that the second portion 72 can expand in the accommodation space 51b when the head 3 of the bone anchoring element 1 is inserted. An outer diameter of the cylindrical portion 77 is slightly smaller than an inner diameter of the passage 51 in the upper part 50 of the receiving part 5 such that the pressure member 7 can slide therein. The pressure member 7 may be insertable from the upper end 5a of the receiving part, whereby during insertion the flexible second portion 72 and the upstanding legs 79a, 79b may be slightly compressed towards each other until the second portion 72 is arranged in the accommodation space 51b and the outwardly directed portions 700a, 700b engage the groove 59a.

The receiving part 5, the pressure member 7, the clamping ring 8, and the bone anchoring element 1, as well as the rod 6, may each be made of bio-compatible materials, for example of titanium or stainless steel, of a bio-compatible alloy, such as NiTi-alloys, for example Nitinol, of magnesium or magnesium alloys, or from a bio-compatible plastic material, such as, for example, polyether ether ketone (PEEK) or poly-l-lactide acid (PLLA). In addition, the parts can be made of the same as or of different materials from one another.

Figures 17A, 17B:
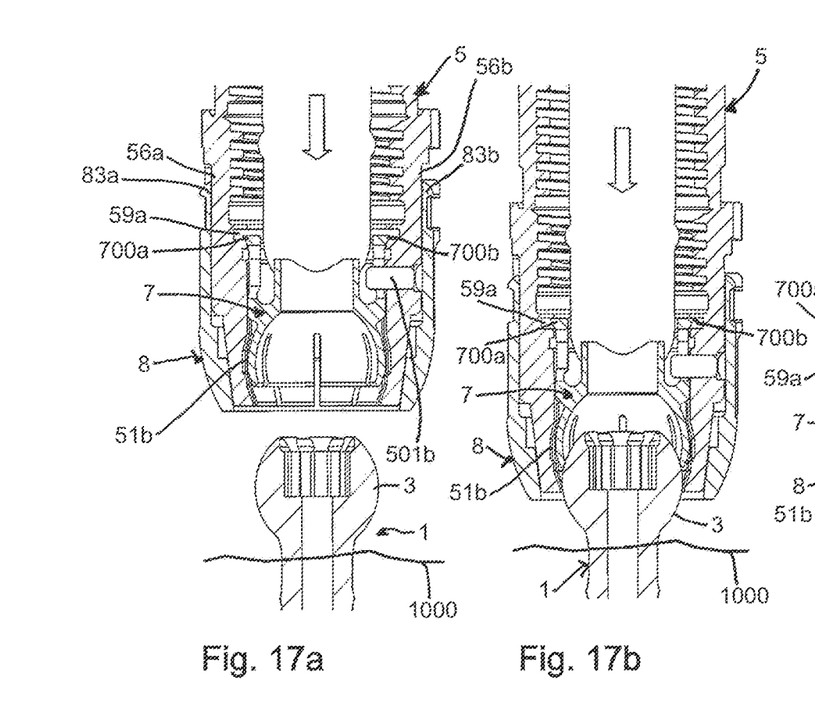
FIGS. 17a to 17d show cross-sectional views of steps of mounting the receiving part and the pressure member to an anchoring element.

Turning now to FIGS. 17a to 17d, the use of the polyaxial bone anchoring device will be explained. First, as illustrated in FIG. 17a, the bone anchoring element 1 may be already inserted into a bone 1000 before the receiving part 5 with the pressure member 7 and the clamping ring 8 is mounted thereon. The receiving part 5 with the pressure member 7 and the clamping ring 8 may be preassembled and the pressure member 7 is secured in the receiving part 5 by the pins 501a, 501b extending through the elongate through-holes 702a, 702b. As shown, the pressure member 7 is in an insertion position in which the outwardly directed end portions 700a, 700b of the legs 79a, 79b extend into the first groove 59a. The clamping ring 8 is in a lower position in which it does not or does only to a small extent exert a compression force onto the head receiving portion 57. The arms 83a, 83b of the clamping ring engage the recessed portions 56a, 56b of the receiving part 5.

Figures 17C, 17D:
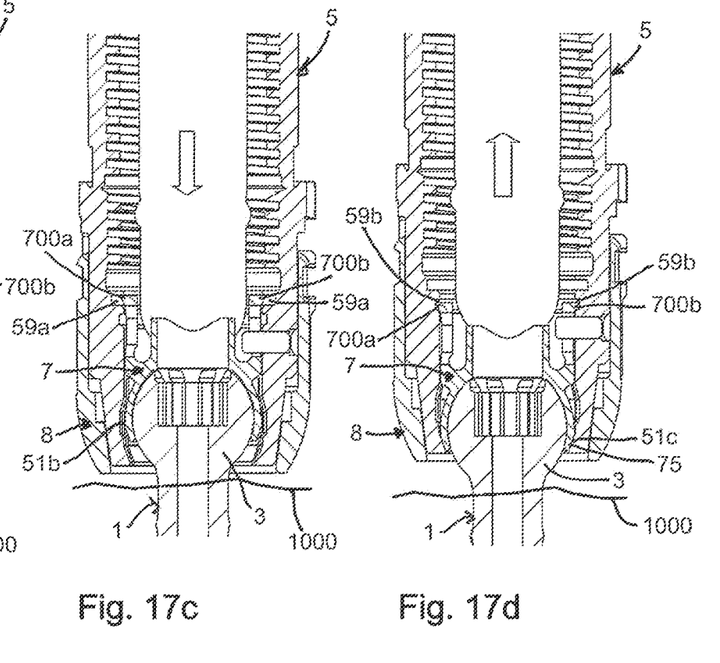

Next, as shown in FIG. 17b, the receiving part 5 is mounted onto the head 3 of the bone anchoring element 1. The head 3 enters the accommodation space through the opening at the second end 5b of the receiving part 5. In this step, the pressure member 7 is moved upwards by the head until the outwardly directed end portions 700a, 700b of the legs 79a, 79b abut against the first stop provided by the upper wall of the first groove 59a As illustrated in FIG. 17c, the head 3 then enters the hollow interior 73 of the pressure member 7. The flexible wall of the second portion 72 of the pressure member 7 snaps over the head so that the second portion 72 encompasses the head 3 laterally. The second portion 72 of the pressure member 7 extends substantially into the accommodation space 51b.

Finally, as depicted in FIG. 17d, the receiving part 5 is pulled upwards with respect to the bone anchoring element 1 and the pressure member 7. Thereby, the outwardly directed portions 700a, 700b of the legs 79a, 79b snap into the second groove 59b. At the same time, the head 3 and the pressure member 7 are pulled into the narrowing portion 51c of the receiving part. By means of this, the head 3 can be clamped by friction. As the head 3 is not locked, the head 3 can still be pivoted in the receiving part 5 by overcoming the frictional force. Depending on the strength of the frictional force, the receiving part 5 may be temporarily held in a specific angular position relative to the bone anchoring element 1. At the same time, the head 3 is prevented from being pulled out of the receiving part 5. Thus, the head 3 is in a pre-locking condition relative to the receiving part 5. The pressure member 7 is prevented from moving upwards by the upper wall of the second groove 59b.

It shall be noted, that the bone anchoring device according to this embodiment can also be used in a pre-assembled manner in which the bone anchoring element 1 is already coupled to the receiving part 5 before it is inserted into the bone.

Figure 18A:
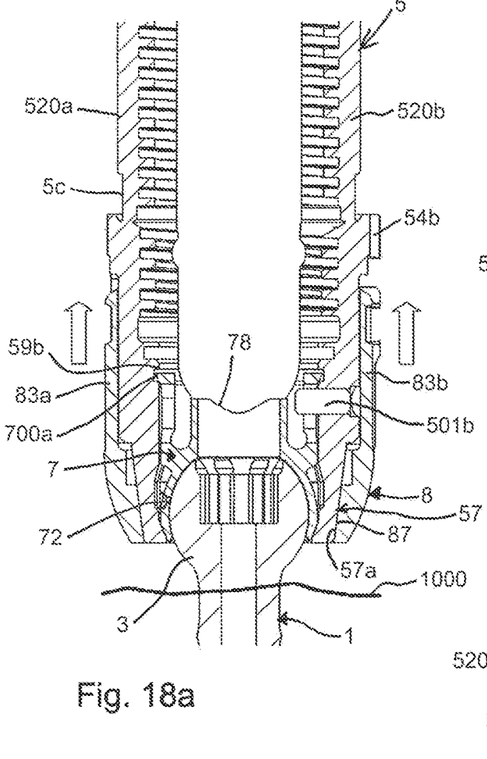
FIG. 18a shows a cross-sectional view of the polyaxial bone anchoring device, wherein the clamping ring assumes a locking position.
Figure 18B:
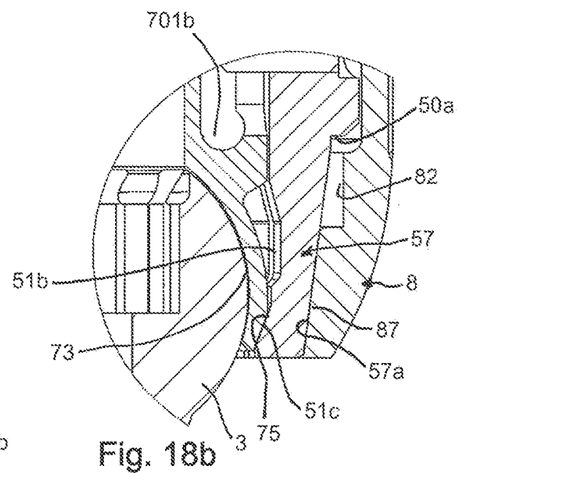
Figure 19:
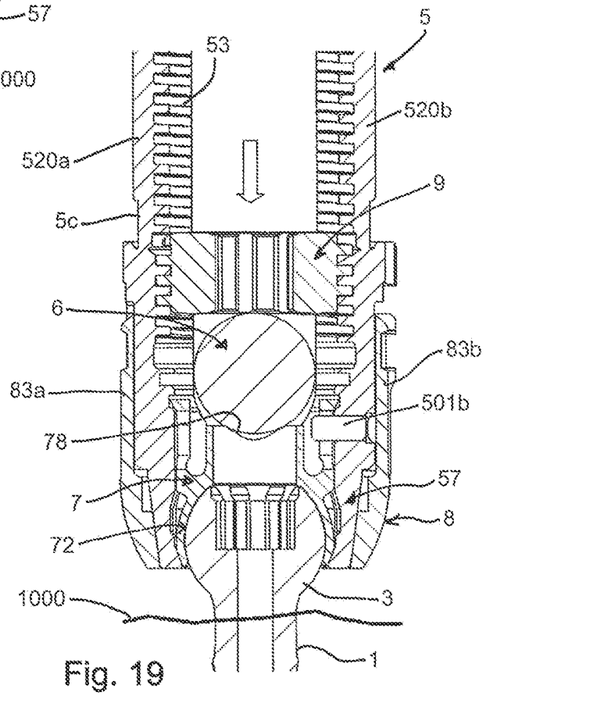
FIG. 19 shows a cross-sectional view of the polyaxial bone anchoring device with an inserted rod and a locking member, wherein the rod and the head are locked.

Referring to FIGS. 18a to 19, locking of the head 3 and of the entire bone anchoring device will be described. As shown in FIGS. 18a and 18b, the head 3 may be locked in the receiving part without the presence of an inserted rod 6 and also without a fixation member 9. To achieve this, the clamping ring is pulled upwards as indicated by the arrows. This can be carried out using an instrument (not shown) that engages the clamping ring 8. Such an instrument may engage, for example, the engagement structure in the form of the ribs 54a, 54b at the receiving part 5 and the engagement structure in the form of the notches 88a, 88b at the clamping ring 8, and displace the clamping ring 8 relative to the receiving part 5. When the clamping ring is pulled upwards, i.e., towards the first end 5a of the receiving part 5, the engagement of the outer tapered surface portion 57a of the head receiving portion 57 of the receiving part 5 and the inner tapered surface portion 87 of the clamping ring 8 increases. The radial force exerted onto the head receiving portion 57 results in a compression of the head receiving portion 57. This in turn results in increased pressure exerted onto the pressure member 7 and the head 3 accommodated therein. When the clamping ring is in its uppermost position, the head 3 is locked. The locking of the head 3 is independent of the presence and/or position of an inserted rod.

The clamping ring 8 may be held in this locking position by self-locking between the engaging conical surfaces. In this case, the clamping ring 8 can be moved out of the locking position only by applying a force greater than the friction force that causes the self-locking, e.g., by using an instrument. Instead or additionally, a holding feature may be provided that holds the clamping ring in the locking position, such as a spring element that removably engages a recess or any other detachable connection between the clamping ring 8 and the receiving part 5.

Finally, as depicted in FIG. 19, when the rod 6 and the fixation element 9 have been inserted, the fixation element 9 is tightened to fix the rod 6. As the rod 6 is supported by the rod support surface 78 of the pressure member 7, tightening of the fixation element 9 in turn presses the pressure member 7 downward against the lower portion 51c of the accommodation space 51b, whereby the locking of the head 3 is further increased and thus the entire device is locked.

In an exemplary surgical operation, first at least two bone anchoring elements 1 are anchored, for example in two adjacent vertebrae. Then the receiving parts 5 are mounted thereon. Once a correct angular position of the head 3 and a correct position of the receiving part 5 relative to the rod 6 has been found, the fixation element 9 is tightened. Repositioning of the rod 6 is possible without loosening the locking of the head 3. With the upper portions 520a, 520b of the legs, it is possible to perform correction steps of the rod position and/or the angular position of the head 3 when the rod is at an elevated position in the recess 52.

Figure 20:
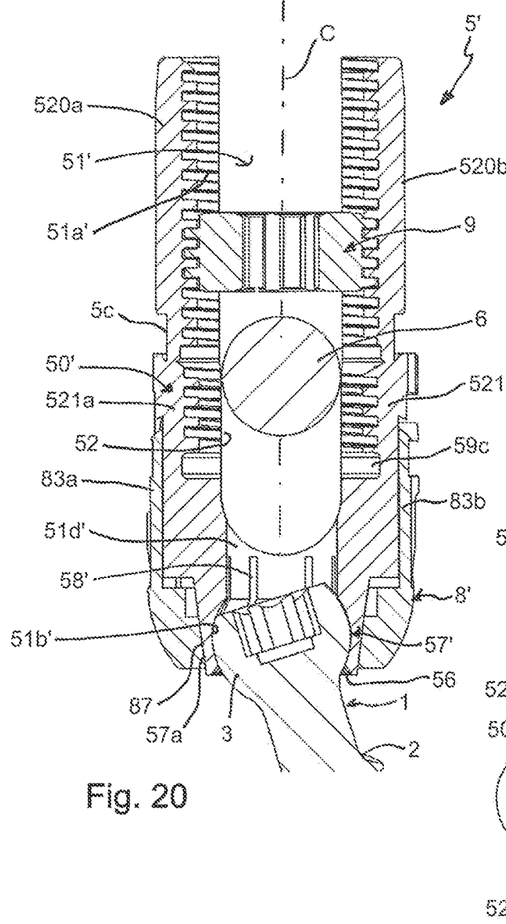
FIG. 20 shows a cross-sectional view of another embodiment of the polyaxial bone anchoring device with an inserted rod and the locking member, wherein the rod is at an elevated position in the rod receiving recess and not fixed.
Figure 21:
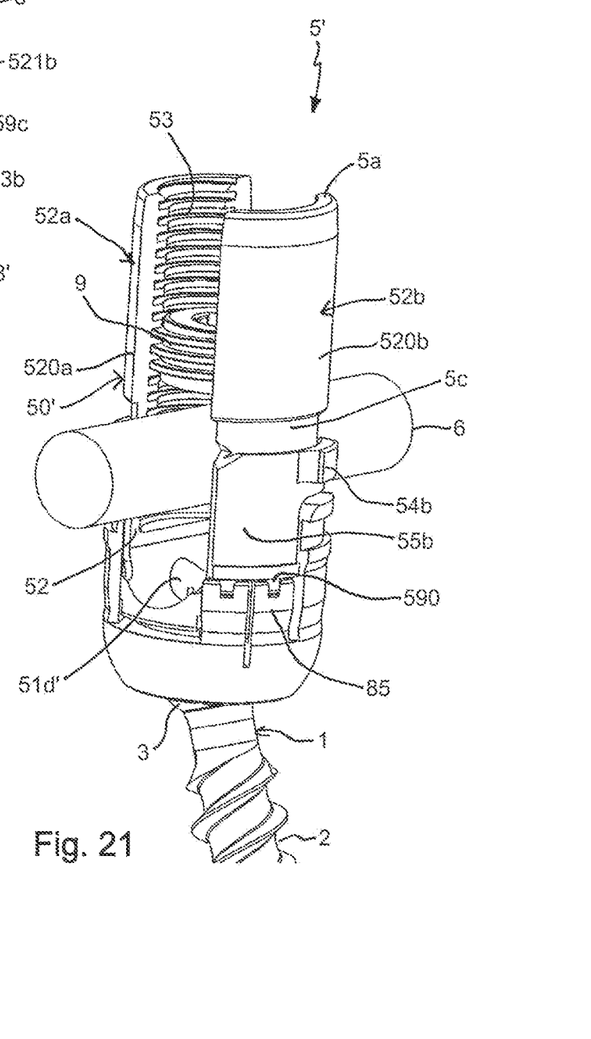
FIG. 21 shows a perspective view of the polyaxial bone anchoring device of FIG. 20 with an inserted rod and the locking member, wherein the rod is movable.

A further embodiment of a bone anchoring device is shown with respect to FIGS. 20 and 21. The embodiment according to FIGS. 20 and 21 differs from the previous embodiment in the design of the receiving part and the clamping ring. Furthermore, this embodiment does not include a pressure member. All other parts are the same or similar to the previously described embodiment, and are indicated with the same reference numerals as in the previous embodiment, and the descriptions thereof will not be repeated. The receiving part 5' includes an upper part 50' and a head receiving portion 57'. A passage 51' extends from the first end 5a to the second end 5b. The passage 51' has a first coaxial bore 51a' that extends from the first end 5a to a distance therefrom and an accommodation space 51b' that extends from the second end 5b to a distance therefrom. The accommodation space 51b' may be spherically-shaped and sized to accommodate and hold the spherical head 3 by means of friction. Between the accommodation space 51b' and the first coaxial bore 51a', a second coaxial bore 51d' may be provided that has a smaller diameter than the first coaxial bore 51a'. This may prevent the inserted head 3 from moving upwards. Slits 58' may be provided in the wall of the accommodation space 51b' to render the head receiving portion 57' flexible. The slits may extend into the region of the second coaxial bore 51d'. An outer surface portion of the head receiving portion 57' may be conically tapering and narrowing towards the second end 5b.

The clamping ring 8' has on each side of the arms 83a, 83b upstanding flexible wall portions 85 with teeth 85a on their free ends that are configured to engage a groove 590 at the receiving part 5' to hold the clamping ring 8' in the locking position. The flexible wall portions 85 are spaced apart from each other in a region offset from the arms 83a, 83b to permit inserting the rod 6 therebetween.

The bone anchoring element 1 is used in a pre-assembled state in which the head 3 has been inserted into the head receiving portion 57' and the clamping ring 8' has been mounted around the head receiving portion 57'. In this state the head 3 is only clamped, not locked and the angular position of the head 3 is adjustable. The rod 6 and the fixation element 9 may be at an elevated position in the recess 52 or may not yet be inserted when the angular position of the head 3 is adjusted. Once the correct angular position of the head 3 has been found, the clamping ring 8' is moved upwards (e.g., using an instrument which is not shown) to compress the head receiving portion 57' due to the inwardly directed force that results from the engagement of the two conical surfaces 57a, 87 of the head receiving portion 57' and the clamping ring 8', respectively, to lock the head 3 in the accommodation space 51b'. The rod is fixed by tightening the fixation element 9.

Further modifications can also be contemplated. The outer surface of the head receiving portion and the inner surface of the clamping ring need not to be tapered, in particular need not to be conically tapered but can also have other shapes wherein the engagement of the two surfaces results in a compression of the head receiving portion by the clamping ring when the clamping ring is moved upwards. More specifically, the shapes of the engaging surfaces need not to be matching shapes. For example, the inner surface of the clamping ring that engages the outer surface of the head receiving portion may also be cylindrical. Also, the clamping ring can have various other designs.

Other engagement structures on the receiving part and/or the clamping ring may also be contemplated that provide a form-fit connection between an instrument and the receiving part or the clamping ring. In some embodiments, the engagement structures may also be provided on only one side of the receiving part and on one side of the clamping ring. The position of the engagement structure may be different in any direction from that shown in the embodiments above.

The bone anchoring device according to other embodiments of the invention can be provided in further modified forms. For example, the head of the bone anchoring element can have any other shape, such as, for example, a cylindrical shape or a spherical shape with flattened sides wherein a monoplanar device is provided that allows pivoting of the anchoring element in a single plane. The head can also be conically shaped or otherwise shaped, with the internal hollow section of the head receiving portion adapted to the specific shape. In a further modification, the flexibility of the head receiving portion may be based on or facilitated by properties of the material, for example, a plastic material may be used, and the slits in the head receiving portion may be fully or partly omitted.

In the pressure member, the upstanding legs may be omitted. Other structures may be provided that prevent the pressure member from escaping during insertion of the head. The pressure member may also be shaped such that it can be inserted from the lower end of the receiving part.

In some embodiments, the head receiving portion can have an inclined open end or can be otherwise asymmetric to allow for a greater angulation of an inserted head in one direction.

The extended tabs on the receiving part can be omitted.

In addition, in some embodiments, other kinds of fixation elements can also be used, for example, non-threaded locking elements that have an alternative advancement structure. In addition, all kinds of bone anchoring devices can be used, such as, for example, nails or bone anchors with barbs.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:
1. A bone anchoring device comprising:
   a bone anchoring element comprising a head and a shank for anchoring in a bone or a vertebra;

a receiving part for coupling a rod to a bone anchoring element, the receiving part having a first end, a second end, a central axis extending through the first and second ends, a recess at the first end for receiving the rod, and a head receiving portion at the second end for accommodating the head of the bone anchoring element;

a pressure member positionable in the receiving part and comprising an engagement surface configured to exert pressure on the head; and a ring configured to be assembled to and movable towards the first end of the receiving part to an uppermost position relative to the receiving part where the ring is configured to directly engage and compress a radially compressible portion of the bone anchoring device to clamp the head in the head receiving portion;

wherein when the ring is assembled to and remains at a same axial position relative to the receiving part, the head is insertable through the second end of the receiving part into the head receiving portion and is restricted from being removed out of the head receiving portion through the second end; and wherein when the head is clamped in the head receiving portion, at least part of the head receiving portion is configured to extend axially below a greatest diameter of the head measured in a direction perpendicular to the central axis.

2. The bone anchoring device of claim 1, wherein the radially compressible portion is formed on the head receiving portion of the receiving part.

3. The bone anchoring device of claim 1, wherein the ring is positionable around the head receiving portion of the receiving part.

4. The bone anchoring device of claim 3, wherein when the ring is at the uppermost position, the ring exerts a force on the head receiving portion to radially compress the head receiving portion.

5. The bone anchoring device of claim 1, wherein the radially compressible portion is fixed axially relative to the first end of the receiving part.

6. The bone anchoring device of claim 1, wherein when the ring is at the uppermost position, the bone anchoring device is configured to assume a locking position where an angular position of the bone anchoring element is locked relative to the receiving part.

7. The bone anchoring device of claim 1, wherein when the head is in the head receiving portion and the locking ring is at the uppermost position, the head is prevented from being removed out of the head receiving portion through the second end.

8. The bone anchoring device of claim 1, wherein when the head is in the head receiving portion and the ring is at the uppermost position, the head is configured to be clamped in the head receiving portion while the recess for the rod remains sufficiently unobstructed for the rod to extend and move therethrough.

9. The bone anchoring device of claim 1, wherein the ring is movable downward from the uppermost position relative to the receiving part to reduce the clamping force on the head.

10. The bone anchoring device of claim 1, wherein the head is held in a seat, and the radially compressible portion is configured to be spaced apart from the seat.

11. The bone anchoring device of claim 10, wherein the seat for the head is formed on the pressure member.

12. The bone anchoring device of claim 11, wherein the ring is configured to compress the radially compressible portion, which in turn is configured to compress the pressure member to clamp the head.

13. A bone anchoring device comprising:

a receiving part for coupling a rod to a bone anchoring element, the receiving part having a first end, a second end, a central axis extending through the first and second ends, a recess at the first end for receiving the rod, and a head receiving portion at the second end for accommodating a head of the bone anchoring element;

a pressure member positionable in the receiving part and comprising an engagement surface configured to exert pressure on the head of the bone anchoring element;

a ring configured to be assembled to and movable towards the first end of the receiving part to an uppermost position relative to the receiving part where the ring is configured to compress a radially compressible portion of the bone anchoring device to clamp the head in the head receiving portion; and at least one additional member positionable radially between the ring and the central axis, wherein an uppermost portion of the at least one additional member is positionable axially above a lowermost portion of the receiving part, and wherein the at least one additional member comprises a surface configured to restrict axial movement of the pressure member relative to the receiving part.

14. The bone anchoring device of claim 13, wherein the radially compressible portion is formed on the head receiving portion of the receiving part.

15. The bone anchoring device of claim 13, wherein the ring is positionable around the head receiving portion of the receiving part.

16. The bone anchoring device of claim 13, wherein the at least one additional member comprises at least one pin that is engageable with the pressure member.

17. The bone anchoring device of claim 13, wherein the at least one additional member is configured to restrict axially upward movement of the pressure member relative to the receiving part.

18. The bone anchoring device of claim 13, wherein the uppermost portion of the at least one additional member is positionable axially above a lowermost portion of the pressure member.

19. The bone anchoring device of claim 13, wherein the at least one additional member is positionable entirely axially above the head of the bone anchoring element when the head is held in the head receiving portion.

20. A bone anchoring device comprising:

a bone anchoring element comprising a head and a shank for anchoring in a bone or a vertebra;

a receiving part for coupling a rod to the bone anchoring element, the receiving part having a first end, a second end, a central axis extending through the first and second ends, a recess at the first end for receiving the rod, and a head receiving portion at the second end for accommodating the head of the bone anchoring element;

a ring configured to be assembled to and movable towards the first end of the receiving part to an uppermost position relative to the receiving part where the ring is configured to compress a radially compressible portion of the bone anchoring device to clamp the head in the head receiving portion while the recess for the rod remains sufficiently unobstructed for the rod to extend and move therethrough;

wherein when the ring is assembled to and remains at a same axial position relative to the receiving part, the head is insertable through the second end of the receiving part into the head receiving portion and is restricted from being removed out of the head receiving portion through the second end; and wherein when the head is clamped in the head receiving portion, at least part of the head receiving portion is configured to extend axially below a greatest diameter of the head measured in a direction perpendicular to the central axis.

21. The bone anchoring device of claim 20, wherein the radially compressible portion is formed on the head receiving portion of the receiving part.

22. The bone anchoring device of claim 20, wherein the ring is positionable around the head receiving portion of the receiving part.

23. The bone anchoring device of claim 20, wherein the radially compressible portion is configured to expand when the head is inserted through the second end of the receiving part into the head receiving portion.

24. The bone anchoring device of claim 20, further comprising a pressure member positionable in the receiving part and comprising an engagement surface configured to exert pressure on the head.

* * * * *